United States Patent
Turchetta et al.

(10) Patent No.: US 7,105,681 B2
(45) Date of Patent: Sep. 12, 2006

(54) PROCESS FOR THE PREPARATION OF SULPHINYL DERIVATIVES BY OXIDATION OF THE CORRESPONDING SULFIDES

(75) Inventors: Stefano Turchetta, Rome (IT); Pietro Massardo, Rome (IT); Angela Tuozzi, Rome (IT)

(73) Assignee: Chemi SPA, Cinisello Balsamo (IT)

( * ) Notice: Subject to any disclaimer, the term of this patent is extended or adjusted under 35 U.S.C. 154(b) by 0 days.

(21) Appl. No.: 11/149,544

(22) Filed: Jun. 10, 2005

(65) Prior Publication Data
US 2006/0014798 A1    Jan. 19, 2006

Related U.S. Application Data

(63) Continuation of application No. PCT/IT02/00826, filed on Dec. 23, 2002.

(51) Int. Cl.
    *C07D 401/12*    (2006.01)
(52) U.S. Cl. .................................... 546/273.7
(58) Field of Classification Search ............. 546/273.7
See application file for complete search history.

(56) References Cited

FOREIGN PATENT DOCUMENTS

WO    WO 01/21617 A1    3/2001
WO    03/097606    * 11/2003

OTHER PUBLICATIONS

Huang, R., et al; "Two Routes to Bis(μ-diphenylphosphino)methane Diplatinum Halides Bridged by Sulfur Monoxide"; *Organometallics*; vol. 18; pp. 5420-5422 (1999).

Vassell, K.A., et al; "Oxidation of Organic Sulfides by Electrophilically-Activated Peroxide: The Catalytic Ability of Methylrhenium Trioxide"; *Inorg. Chem.*; vol. 33; pp. 5491-5498 (1994).

Adam. W., et al; "Chemoselective Methyltrioxorhenium (VII)-Catalyzed Sulfoxidations with Hydrogen Peroxide"; *Tetrehedron*; vol. 50, No. 46; pp. 13121-13124 (1994).

* cited by examiner

Primary Examiner—Patricia L. Moore
(74) *Attorney, Agent, or Firm*—Nixon & Vanderhye

(57) ABSTRACT

Process for preparing sulfinyl derivatives of Formula 2, useful as inhibitors of gastric acid secretion, comprising the selective oxidation of the corresponding sulfides of formula 1, as represented in the following scheme

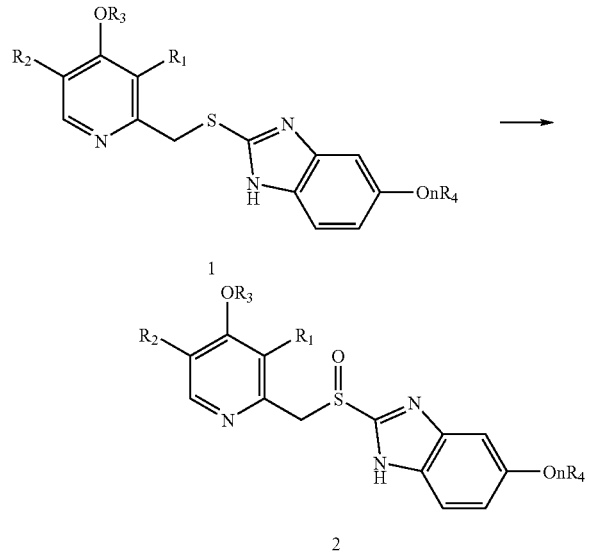

The oxidation is performed with hydrogen peroxide in the presence of low amounts of a rhenium compound as catalyst, at a temperature from 0° C. to room temperature.

18 Claims, No Drawings

PROCESS FOR THE PREPARATION OF SULPHINYL DERIVATIVES BY OXIDATION OF THE CORRESPONDING SULFIDES

This application is a continuation of Application No. PCT/IT2002/00826, filed Dec. 23, 2002, the entire content of which is hereby incorporated by reference in this application.

FIELD OF THE INVENTION

The present invention relates to a mild and industrially applicable process for preparing sulfinyl derivatives, useful as inhibitors of gastric acid secretion, by selective oxidation of the corresponding sulfides, in particular by oxidation with hydrogen peroxide in the presence of a rhenium compound as catalyst.

BACKGROUND OF THE INVENTION

A whole class of gastric Na/K pump inhibitors, widely used as antiulcer drugs, are benzimidazole compounds containing in their skeleton a sulfoxide moiety. Omeprazole, Lansoprazole, Pantoprazole and Rabeprazole are the most famous members of this class of compounds and several patents have appeared dealing with their synthesis.

Whatever the staring materials are, the final step of their preparation is invariably the oxidation of the corresponding sulfide 1, as represented in the following Scheme 1:

Scheme 1

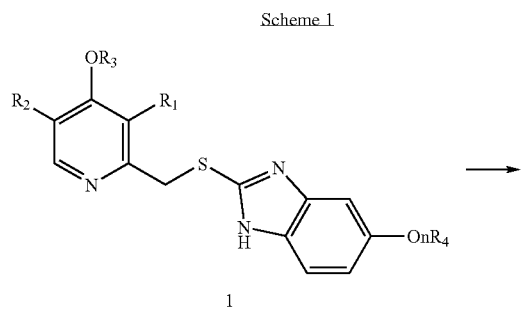

1

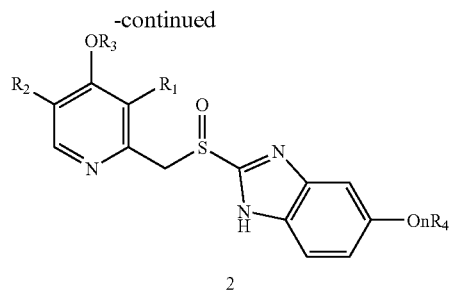

2 in which each substituent of the above formulae has, for the drugs just mentioned, the meaning reported here below:

| | | |
|---|---|---|
| Omeprazole | 2a | $R_1=R_2=R_3=R_4=Me$; n=1 |
| Lansoprazole | 2b | $R_1=Me$; $R_2=R_4=H$; $R_3=CH_2CF_3$; n=0 |
| Pantoprazole | 2c | $R_1=OMe$; $R_2=H$; $R_3=Me$; $R_4=CHF_2$; n=1 |
| Rabeprazole | 2d | $R_1=Me$; $R_2=R_4=H$; $R_3=CH_2CH_2CH_2OCH_3$; n=0 |

So far, several methods for performing the above oxidation have been described in the literature. Such methods use different oxidizing agents and/or conditions of reaction (see as an example WO99/47514 and the references cited therein).

Particularly relevant for the present invention are those oxidations that use hydrogen peroxide as oxidizing agent, in the presence of a transition metal compound as catalyst. For example EP302720 describes the use of vanadium catalysts for the oxidation of sulfides 1 with hydrogen peroxide, whereas ES2036948 claims as catalyst for the same transformation phosphotungstic acid, ammonium molibdate, sodium tungstate, phosphomolibdic acid and silicotungstic acid. ES2105953 specifically claims phosphomolibdic acid for this transformation.

All these oxidation methods show serious problems of impurity formation due to overoxidation As a matter of fact overoxidation of 1 can form byproducts such as the sulfone 3 or the N-oxides 4 e 5, as represented in the following Scheme 2:

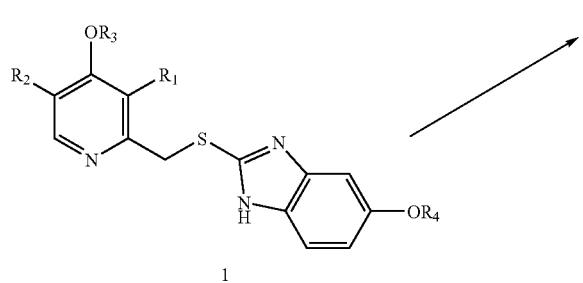

1

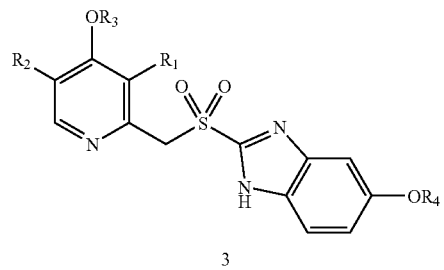

3

-continued

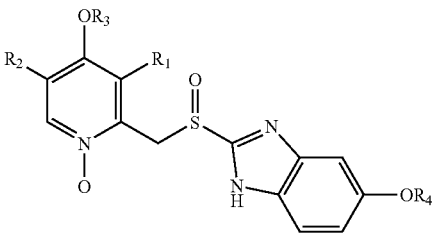

4

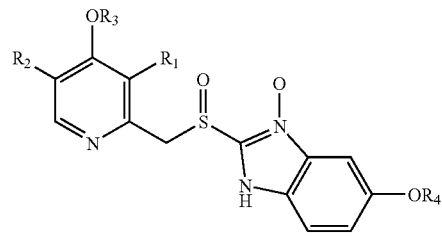

5

Other examples of the same kind of oxidation are disclosed in WO02/074766 and WO01/21617.

In particular, WO02/074766 describes the preparation of Lansoprazole from the corresponding sulfide through the reaction of hydrogen peroxide catalyzed by phenylseleninic acid. In this case the use of a toxic selenium catalyst, combined with that of halogenated solvents as reaction media, limits the industrial applicability of the process.

On the other hand, WO01/21617 discloses the use of the same oxidant but in the presence of a different catalyst, namely MeReO$_3$, in an alcoholic medium.

Unfortunately, even if this method is very good as regards selectivity, it is hardly applicable on industrial scale, both for the large quantities of very expensive catalyst employed and for the low temperatures at which the reaction has to be performed. In fact, according to the above patent application, it is possible to achieve the good yields and the high purity of the final sulfoxide reported therein, only by keeping the amount of catalyst and the reaction temperature within specific values, rather disadvantageous from the industrial point of view.

As stated in the description, the catalyst may be used in an amount from 0.1 to 10 moles % but, preferably, from 1 to 5 mole % (see page 12, lines 18–20) with respect to the starting material In addition, the amount of catalyst effectively used in example 1—the only one according to the invention—is about 4 mole %. In the same patent application it is stated that " . . . when the methyltrioxorhenium catalyst was used at the amount of 1 mole % or less, yield was decreased" (see page 18, lines 11–13).

As a matter of fact, the whole application teaches that an amount of catalyst greater than 1 mole % is required for obtaining satisfactory results.

But even more relevant for the present discussion are the temperature requirements.

In fact the description of WO01/21617 states that the oxidizing reaction is carried out at a temperature from −40° C. to 0° C., preferably from −30° C. to −15° C. (see page 13, lines 4 and 5) while all the examples are performed at a temperature of −20 to −30° C.

The main teaching that a skilled in the art could have got by reading the patent application in object is that a temperature lower than 0° C. was necessary in order to reduce the formation of by-products and achieve good results. In other words, the content of WO01/21617 would have seriously discouraged any attempt to perform the same oxidation at a higher temperature and with a lower amount of catalyst.

In conclusion, in view of the above discussion on the relevant prior art, it would be highly desirable to dispose of a selective and industrially feasible method of oxidation of sulfide 1 to sulfoxide 2, that would produce satisfactory yields of a highly pure final product, by using a very low amount of catalyst and by performing said oxidation at a temperature compatible with standard industrial equipments.

Notwithstanding the opposite teaching of the closest art (WO01/21617), it has now been found that the oxidation of sulfide 1 to the desired sulfoxides 2 disclosed in said patent application can be run with good selectivity and recovery of the desired product by using lower catalyst loadings and temperatures higher than 0° C. The opportunity of lowering the catalyst loading is particularly advantageous both in terms of reduced contamination of the final product with heavy metals and in terms of cost of the catalyst. On the other hand, the chance of performing the reaction at higher temperatures avoids the need of special expensive low temperature equipments, allowing the use of ordinary industrial reactors for the synthesis. As a matter of fact, the present process represents a cheaper and industrially practicable advantageous alternative for preparing the class of compounds in object.

SUMMARY OF THE INVENTION

Therefore it is the object of the present invention a process for preparing a sulfinyl derivative of formula 2

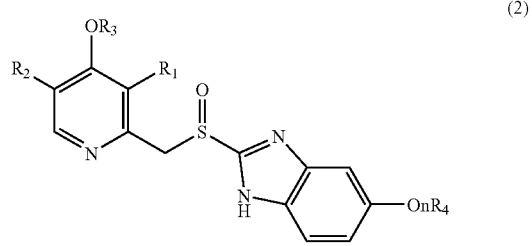

(2)

in which
$R_1$ represents hydrogen, a $(C_1-C_4)$-alkyl or a $(C_1-C_4)$-alkoxy group,
$R_2$ represents hydrogen or a $(C_1-C_4)$-alkyl group,
$R_3$ represents a $(C_1-C_4)$-alkyl group, a fluorinated $(C_1-C_4)$-alkyl group or a $(C_1-C_4)$-alkoxy-$(C_1-C_4)$-alkyl group,
$R_4$ represents hydrogen or a $(C_1-C_4)$alkyl group, and
n represents an integer selected between 0 and 1;

which comprises the step of oxidizing a sulfide compound of formula 1

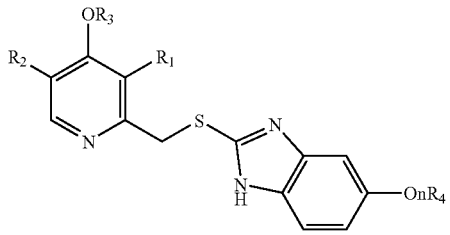

(1)

in which $R_1$, $R_2$, $R_3$, $R_4$ and n have the above meanings, with hydrogen peroxide as oxidizing agent in the presence of a rhenium compound as catalyst, characterized in that said catalyst is used in an amount from 0.01 to 0.5 moles % with respect to the sulfide 1 and the temperature of the oxidation reaction is kept from 0° C. to room temperature.

DESCRIPTION OF THE INVENTION

The operative description of the process object of the present invention is the following: the sulfide 1 is dissolved in a solvent, then the selected amount of rhenium compound is added to the solution, the temperature of the mixture is brought to the desired value and hydrogen peroxide is added. The reaction mixture is allowed to react until completion, then water is added to precipitate the bulk of the product; the solid is then filtered, washed with additional water and, optionally, crystallized.

The starting material of the present process, namely the sulfide 1, may be prepared according to any method described in the cited prior art or according to the references reported therein (see as an example WO99/47514).

In the present description, the substituent groups of the compounds of formula 1 and 2, as reported above, have to be construed as follows:
a $(C_1-C_4)$-alkyl group means a group such as methyl, ethyl, n-propyl, i-propyl n-butyl, i-butyl t-butyl;
a $(C_1-C_4)$-alkoxy group means a group such as methoxy, ethoxy, n-propoxy, i-propoxy, n-butoxy, i-butoxy, t-butoxy;
a fluorinated $(C_1-C_4)$-alkyl group means a $(C_1-C_4)$-alkyl group, as defined above, in which one or more hydrogen are substituted by fluorine atoms such as trifluoromethyl, trifluoroethyl, difluoromethyl, monofluoromethyl;
a $(C_1-C_4)$-alkoxy-$(C_1-C_4)$-alkyl group means a $(C_1-C_4)$-alkoxy group, as defined above, linked to a $(C_1-C_4)$-alkyl group, as defined above, such as methoxymethyl, ethoxyethyl methoxyethyl, methoxypropyl.

Preferred starting sulfide of formula 1 are the precursor of the compounds 2a (Omeprazole; $R_1=R_2=R_3=R_4=Me$; n=1), 2b (Lansoprazole; $R_1=Me$; $R_2=R_4=H$; $R_3=CH_2CF_3$; n=0), 2c (Pantoprazole; $R_1=OMe$; $R_2=H$; $R_3=Me$; $R_4=CHF_2$; n=1) and 2d (Rabeprazole; $R_1=Me$; $R_2=R_4=H$; $R_3=H_2CH_2CH_2OCH_3$; n=0).

The solvent used in the present synthesis may be any linear or branched $(C_1-C_6)$ alcohol such as methanol ethanol isopropanol, n-butanol t-butanol, and the like, a ketone such as acetone or methyl-t-butylketone, an ester such as ethyl acetate, an ether, such as ethylether, i-propylether, tetrahydrofuran or an amide, such as formamide, dimethylformamide, dimethylacetamide, preferably an alcohol more preferably a water soluble alcohol selected among methanol, ethanol isopropanol t-butanol and even more preferably methanol. The water miscible solvents, especially the alcoholic solvents, may be used alone or in admixture with water.

The temperature at which the reaction is performed generally ranges from 0° C. to room temperature, more preferably from 0° C. to 10° C., even more preferably from 3° C. to 7° C.

Examples of the rhenium compound used as the catalyst in the practice of the present invention include methyltrioxorhenium, ethyltrioxorhenium, $Re(PPh_3)_2OCl_3$ and the like, preferably methyltrioxorhenium or ethyltrioxorhenium, most preferably methyltrioxorhenium. These catalysts are commercially available, for example they may be purchased from Aldrich or from Strem.

The amount of said rhenium catalyst may range from 0.01 to 0.5 moles % with respect to the sulfide 1, preferably from 0.05 to 0.3 moles % and more preferably from 0.07 to 0.2 moles %.

The oxidizing agent, namely hydrogen peroxide, is generally used as an aqueous solution having a concentration by weight from 30 to 60%, in an amount usually ranging from 1 to 1.5 equivalents, preferably from 1.1 to 1.3 equivalents, with respect to the starting sulfide 1.

The reaction mixture is allowed to react until completion, preferably until the starting material is lower than 2%, then water is added in an amount suitable for precipitating the bulk of the product; the resultant solid is filtered and washed with additional water.

This raw material, whose yields generally range from 90 to 95%, may be further purified, preferably by crystallization.

Said crystallization is generally performed by using aqueous mixtures of ethanol, methanol, isopropanol, t-butanol or acetone, preferably with mixture of water and ethanol, more preferably with 1:9 mixture (v/v) of water and ethanol.

The present process is preferably used for the preparation of sulfinyl derivatives of formula 2 selected among 2a (Omeprazole; $R_1=R_2=R_3=R_4=Me$; n=1), 2b (Lansoprazole; $R_1=Me$; $R_2=R_4=H$; $R_3=CH_2CF_3$; n=0), 2c (Pantoprazole; $R_1=OMe$; $R_2=H$; $R_3=Me$; $R_4=CHF_2$; n=1) and 2d (Rabeprazole; $R_1=Me$; $R_2=R_4=H$; $R_3=CH_2CH_2CH_2OCH_3$; n=0).

In a preferred embodiment of the present process the sulfide 1, precursor of Omeprazole 2a, Lansoprazole 2b, Pantoprazole 2c or Rabeprazole 2d, is dissolved in methanol, then from 0.07 to 0.2 moles % of methyltrioxorhenium are added to the solution, the temperature of the mixture is brought to about 5° C. and from 1.1 to 1.3 equivalents of an about 33% by weight aqueous solution of hydrogen peroxide are added. The reaction mixture is kept at the same temperature and allowed to react until completion. Cold water is finally added to precipitate the bulk of the product and the mixture is further stirred at the same temperature. The solid thus precipitated is then filtered, washed several times with additional cold water and, preferably, crystallized from a 1:9 mixture (v/v) of water and ethanol.

The following examples are reported to better explain the present invention and do not represent a limitation of the invention itself.

EXPERIMENTAL PART

Example 1

Synthesis of 2-[[[3-methyl-4-(2,2,2-trifluoroethoxy)-pyridinyl]methyl]thio]-1H-benzimidazole (Lansoprazole sulfide, 1b)

To a stirred suspension of 100 g of 4-(2,2,2)-trifluoroethoxy-3-methyl-2-chloromethyl-pyridine hydrochloride and 54.4 g of 2-mercapto-benzimidazole at 10° C. in 500 ml of methanol, 125.6 g of a 30% by weight aqueous solution of NaOH are added at such a rate as to maintain the internal temperature within 35° C. The temperature of the mixture is then brought to 20÷25° C. and is kept for additional 4 hours in these conditions. Then 1000 ml of deionized water are added, causing the thickening of the precipitate. The pH of the suspension is adjusted to 9 with HCl 33% in water and the mixture is then cooled to 5° C. and maintained for 1 hour.

The precipitate obtained is filtered and washed with water to obtain 235 g of a wet product which once dried weighs 124.5 g and has an HPLC purity >99%. Yield 97%.

Example 2

Synthesis of 2-[[[3-methyl-4-(2,2,2-trifluoroethoxy)-2-pyridinyl]methyl]sulfinyl]-1H-benzimidazole (Lansoprazole, 2b)

In a 1-liter flask equipped with dropping funnel and mechanical stirring 50 g (0.142 moles) of Lansoprazole sulfide, 35.0 mg (0.00014 moles) of methyltrioxorhenium (Aldrich) and 500 ml of methanol are charged. The temperature of the solution is brought to 5° C., and then 17.8 g (0.173 moles) of a 33% (v/v) aqueous solution of hydrogen peroxide are added. The mixture is maintained at 5° C. for 4 hours, then 1000 ml of cold deionized water are added, whereby a dense precipitate forms. The mixture is stirred for 1 additional hour at 5° C. and is then filtered on a Buchner, the cake is washed with 3×100 ml of cold deionized water and is discharged. The wet solid weighs 59.5 g. A 1 g sample is collected and dried under vacuum (50 mmHg) at 40° C. for 12 hours, which loses 16.5% of its weight. The yield of crude product is thus 95%. The amount of residual water in the crystalline solid is calculated through the Karl-Fischer method and the solid is then recrystallised, talking into account the amount of residual water, from 8 volumes of a 9:1 mixture of ethanol and water. The yield of the crystallized, dried product starting from the sulfide is 75%, the purity of the product is >99.5% (HPLC).

Example 3

Synthesis of 2-[[[3-methyl-4-(2,2,2-trifluoroethoxy)-2-pyridinyl]methyl]sulfinyl]-1H-benzimidazole (Lansoprazole, 2b)

The experiment described in example 1 was repeated on the same amount of sulfide, hydrogen peroxide and methanol, using 17.5 mg (0.00007 moles) of methyltrioxorhenium as catalyst.

After workup and crystallization, 39.0 g of the desired material (yield 74%, HPLC purity >99.5%) are obtained.

Example 4

Synthesis of 5-methoxy-2-[[(4-methoxy-3,5-dimethyl-2-pyridinyl)methyl]sulfinyl]-1H-benzimidazole (Omeprazole, 2a)

The experiment described in example 2 was repeated using 46.8 g of 5-methoxy-2-[[(4-methoxy-3,5 dimethyl-2-pyridinyl)methyl]thio]-1H-benzimidazole as substrate instead of Lansoprazole sulfide. 39.2 g of crystallized Omeprazole are isolated after crystallization and drying (yield 80%).

Example 5

Synthesis of 2-[[[4-(3-methoxypropoxy)-3-methyl-2-pyridinyl]methyl]sulfinyl]-1H-benzimidazole (Rabeprazole, 2d)

The experiment described in example 2 was repeated using 48.8 g of 2-[[[4-(3-methoxypropoxy)-3-methyl-2-pyridinyl]methyl]thio]-1H-benzimidazole as substrate instead of Lansoprazole sulfide. 38.3 g of crystallized Rabeprazole are isolated after crystallization and drying (yield 75%).

Example 6

Synthesis of 5-(difluoromethoxy)-2-[[(3,4-dimethoxy-2-pyridinyl)methyl]sulfinyl]-1H-benzimidazole (Pantoprazole, 2c)

The experiment described in example 2 was repeated using 52.2 g 5-(difluoromethoxy)-2-[[(3,4-dimethoxy-2-pyridinyl)methyl]thio]-1H-benzimidazole as substrate instead of Lansoprazole sulfide. 42.3 g of crystallized Pantoprazole are isolated after crystallization and drying (yield 78%).

the invention claimed is:

1. A process for preparing a sulfinyl derivative of formula 2

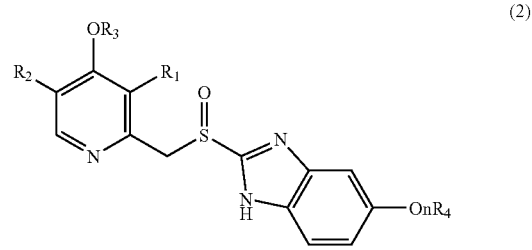

in which
R$_1$ represents hydrogen, a (C$_1$–C$_4$)-alkyl or a (C$_1$–C$_4$)-alkoxy group,
R$_2$ represents hydrogen or a (C$_1$–C$_4$)-alkyl group,
R$_3$ represents a (C$_1$–C$_4$)-alkyl group, a fluorinated (C$_1$–C$_4$)-alkyl group or a (C$_1$–C$_4$)-alkoxy-(C$_1$–C$_4$)-alkyl group,
R$_4$ represents hydrogen or a (C$_1$–C$_4$)-alkyl group, and
n represents an integer selected between 0 and 1;
which comprises the step of oxidizing a sulfide compound of formula 1

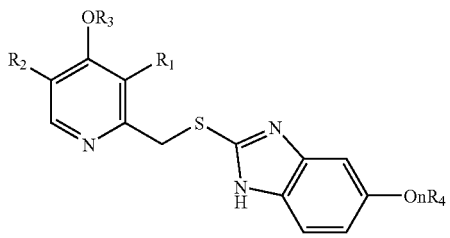

(1)

in which $R_1$, $R_2$, $R_3$, $R_4$ and n have the above meanings, with hydrogen peroxide as oxidizing agent in the presence of a rhenium compound as catalyst, wherein said catalyst is used in an amount from 0.01 to 0.5 moles % with respect to the sulfide 1 and the temperature of the oxidation reaction is kept from 0° C. to room temperature.

2. The process according to claim 1 in which said rhenium compound is selected from the group consisting of methyltrioxorhenium, ethyltrioxorhenium, and $Re(PPh_3)_2OCl_3$.

3. The process according to claim 1 in which the amount of said rhenium catalyst, with respect to the sulfide 1 ranges from 0.01 to 0.5 moles %.

4. The process according to claim 1 in which said oxidation reaction is performed at a temperature from 0° C. to 10° C.

5. The process according to claim 1 in which said oxidation is performed in a solvent selected from the group consisting of linear or branched ($C_1$–$C_6$) alcohols, ketones, esters, ethers and amides.

6. The process according to claim 5 in which said solvent is a water-soluble alcohol selected from the group consisting of methanol, ethanol, isopropanol, and t-butanol.

7. The process according to claim 1 in which the oxidizing agent is an aqueous solution of hydrogen peroxide having a concentration by weight from 30 to 60%, in an amount with respect to the starting sulfide 1 that ranges from 1 to 1.5 equivalents.

8. The process according to claim 1 further comprising the crystallization of the raw product from aqueous mixtures of ethanol, methanol, isopropanol, t-butanol or acetone.

9. The process according to claim 8 in which said mixture is a 1:9 mixture (v/v) of water and ethanol.

10. The process according to claim 1 for the preparation of a sulfinyl derivative of formula 2 selected from the group consisting of 2a (Omeprazole; $R_1=R_2=R_3=R_4=Me$; n=1), 2b (Lansoprazole; $R_1=Me$; $R_2=R_4=H$; $R_3=CH_2CF_3$; n=0), 2c (Pantoprazole; $R_1=OMe$; $R_2=H$; $R_3=Me$; $R_4=CHF_2$; n=1) and 2d (Rabeprazole; $R_1=Me$; $R_2=R_4=H$; $R_3=CH_2CH_2CH_2OCH_3$; n=0).

11. The process according to claim 1 in which said rhenium compound is methyltrioxorhenium.

12. The process according to claim 1 in which the amount of said rhenium catalyst, with respect to the sulfide 1 ranges from 0.05 to 0.3 moles %.

13. The process according to claim 1 in which the amount of said rhenium catalyst, with respect to the sulfide 1 ranges from 0.07 to 0.2 moles %.

14. The process according to claim 1 in which said oxidation reaction is performed at a temperature from 3° C. to 7° C.

15. The process according to claim 5 in which said water-soluble alcohol is optionally in admixture with water.

16. The process according to claim 5 in which said water-soluble alcohol is methanol.

17. The process according to claim 1 in which the oxidizing agent is an aqueous solution of hydrogen peroxide having a concentration by weight from 30 to 60%, in an amount with respect to the starting sulfide 1 that ranges from 1.1 to 1.3 equivalents.

18. The process according to claim 1 further comprising the crystallization of the raw product from a mixture of water and ethanol.

* * * * *